United States Patent [19]

Coles et al.

[11] Patent Number: 5,531,729

[45] Date of Patent: Jul. 2, 1996

[54] ELASTIC NET-LIKE SUBSTRATE HAVING A LAYER OF FIBERS PRE-BONDED THERETO FOR USE IN AN ABSORBENT ARTICLE

[75] Inventors: Peter Coles, Kelkheim Fischbach; Attila Tamer, Schwalbach/Ts., both of Germany

[73] Assignee: The Procter & Gamble Company, Cincinnati, Ohio

[21] Appl. No.: 307,674

[22] PCT Filed: Mar. 11, 1993

[86] PCT No.: PCT/US93/02151

§ 371 Date: Sep. 22, 1994

§ 102(e) Date: Sep. 22, 1994

[87] PCT Pub. No.: WO93/18729

PCT Pub. Date: Sep. 30, 1993

[30] Foreign Application Priority Data

Mar. 24, 1992 [EP] European Pat. Off. .............. 92870047

[51] Int. Cl.⁶ .................................................... A61F 13/15
[52] U.S. Cl. ........................ 604/384; 604/373; 604/385.2
[58] Field of Search .................................. 604/358, 367, 604/373, 378, 384, 385.2; 428/284

[56] References Cited

U.S. PATENT DOCUMENTS

| | | |
|---|---|---|
| 4,407,284 | 10/1983 | Pieniak ................................... 604/385 |
| 4,450,026 | 5/1984 | Pieniak et al. .......................... 156/164 |
| 4,606,964 | 8/1986 | Wideman . | |
| 4,968,313 | 11/1990 | Sabee .................................... 604/385.2 |
| 4,977,011 | 12/1990 | Smith . | |
| 5,334,446 | 8/1994 | Quantrille et al. ...................... 428/284 |
| 5,352,216 | 10/1994 | Shiono et al. .......................... 604/312 |

FOREIGN PATENT DOCUMENTS 803714  1/1969  Canada ................................. 604/384

Primary Examiner—Michael J. Milano
Attorney, Agent, or Firm—Kevin C. Johnson; Steven W. Miller; E. Kelly Linman

[57] ABSTRACT

In an absorbent article, such as a diaper or incontinence briefs, an elastic member comprising a net-like elastic substrate to which fibers are pre-bonded provides for a breathable elastic for use as a side- a waist- or leg elastic. The fibers that are bonded to the net-like substrate, for instance by hydro-entangling, ensure a soft and comfortable contact with the wearer's skin. In the side panels of the absorbent article, the elastic members have a large freedom of stretch without buckling taking place, thus reducing chances of leakage. When the elastic member is located between the topsheet and the backsheet, a strong connection of topsheet to backsheet is established using a relatively small amount of adhesive. When the topsheet is physically deformed to impart stretchability, the fibers of the elastic member form a soft and resilient layer and prevent direct contact of the elastic member and the user's skin in case of thinning of the topsheet.

6 Claims, 2 Drawing Sheets

ELASTIC NET-LIKE SUBSTRATE HAVING A LAYER OF FIBERS PRE-BONDED THERETO FOR USE IN AN ABSORBENT ARTICLE

FIELD OF THE INVENTION

The invention relates to an absorbent article comprising a topsheet, a liquid impervious backsheet associated with the topsheet, an absorbent core disposed between the topsheet and the backsheet, a periphery of the absorbent article comprising two longitudinal sides and two lateral sides extending transversely to the longitudinal sides, and an elastic member connected to a body-facing side of the backsheet, the elastic member comprising a net-like substrate of interconnected elastic strands.

The invention also relates to an absorbent article comprising a liquid impervious backsheet, a periphery of which comprises two longitudinal sides and two lateral sides extending transversely to the longitudinal sides, the longitudinal sides each comprising a first end part and a second end part, the end parts of each longitudinal side being mutually joined in a respective side panel area so that the lateral sides form an endless waistband or a part thereof, the part of each longitudinal side that is located between the end parts, forming a respective endless legcuff or a part thereof, an absorbent core disposed on a body-facing side of the backsheet and an elastic member which is connected to the body-facing side of the backsheet, the elastic member comprising a net-like substrate of interconnected elastic strands.

BACKGROUND OF THE INVENTION

Such an absorbent article is known from the American patent U.S. Pat. No. 4,407,284.

In this patent a net-like elastic member is disclosed having longitudinal strands that are intermittently mutually connected by a number of transverse strands. The elastic member is placed between the backsheet and the topsheet of an absorbent article, in particular a diaper. The elastic substrate is placed in parallel with and in the proximity of the longitudinal sides to provide an elastic leg cuff, or in parallel with and in the proximity of the lateral sides to provide an elastic waist feature. The elastic member is placed between the topsheet and the backsheet in its streched condition, the topsheet being laminated to the backsheet through the the open areas in the elastic member. Upon relaxation of the elastic member, the topsheet and the backsheet are gathered only for those parts of the elastic member that are transversely connected. The modulus of elasticity at 100% elongation of the elastic member, that can be made of any strechable film material of a preferred thickness of between 0.13 mm and 0.50 mm, preferably lies between 1.4 and 140 Kgcm$^{-2}$.

An absorbent article of the above mentioned kind, can at the areas where the elastic member is placed between the topsheet and the backsheet, be relatively uncomfortable to the skin because the glue, fixing the topsheet to the backseet, can reduce softness or the fibrous nature of the topsheet. Furthermore, the direction of stretch is confined to the longitudinal direction of the elastic member, the bonding of the topsheet to the backsheet allowing no stretch perpendicular thereto.

OBJECTS OF THE INVENTION

It is an object of the invention to provide for an absorbent article comprising an elastic member having good fluid-handling properties and being comfortable during use.

It is another object of the invention to provide for an absorbent article comprising an elastic member giving an improved fit of the absorbent article during use.

It is another object of the invention to provide for an elastic member that can be placed on a body-facing side of the backsheet, or between the topsheet and the backsheet, in a non-stretched condition and which can be firmly attached to the topsheet or the backsheet using a relatively small amount of glue.

It is again anoter object of the invention to provide for an absorbent article comprising an elastic member which, when placed between the topsheet and the backsheet, allows for good adhesion thereto while at the same time enabling a relatively large freedom of movement of the combined topsheet and backsheet.

SUMMARY OF THE INVENTION

An absorbent article according to the invention is characterized in that at least one layer of fibers is pre-bonded to a body-facing side of the substrate.

Because the fibrous nature of the surface of the elastic member that is located adjacent to the skin of the wearer of the absorbent article, provides for sufficient resiliency and bulk, it is comfortable to the wearer. Contrary to the elastic member disclosed in the prior art, wherein the topsheet is directly glued to the backsheet through the openings of the elastic substrate, the backsheet and the elastic substrate are isolated from the skin of the wearer by the fibers.

The bulk of the elastic member in the absorbent article according to the invention, can be varied to a large extent, independently from the tensile properties of the elastic member, by bonding more or less fibers to the elastic substrate.

The combined backsheet and elastic member according to the invention, are stretchable in a relatively large number of directions, without serious wrinkling or buckling of the backsheet and the elastic member occurring. Hereby the fit of the absorbent article is improved and chances of leakage along the elastic member are reduced.

The presence of the layer of fibers between the wearer's skin and the backsheet, further allows moisture entrapped between the user's skin and the elastic member, such as sweat, to evaporate via the fibers. Thus chances of skin irritation are reduced and comfort during wearing is increased.

Elastic substrates comprising an elastic web or net, to which staple textile fibers are hydraulically entangled, are known from the American patent U.S. Pat. No. 4,775,579, which is hereby incorporated by reference. The elastic strands of the web can be made of ethylene-polybutylene copolymers, poly(ethylene-butylene) polystyrene block copolymers, polyadipate esters, polyurethanes, polyester elastomeric polymers and the like. The fibers, which need not be elastic, can be made of cotton, rayon, polyolefins, polyamides, polyesters, acrylic fibers or wool.

An embodiment of an absorbent article according to the invention is characterized in that the absorbent article is comprised between the topsheet and the backsheet.

For certain absrobent articles such as diapers, the topsheet and the backsheet are coextensive and have a common periphery. Unlike in absorbent articles such as training pants or adult incontinence briefs, in which in general the backsheet is larger than the topsheet, the elastic members in such diapers are comprised between the topsheet and the backsheet. The fibers which are pre-bonded to the elastic substrate, for instance by hydro-entangling, by needling or by any other means of attachment such as fusion bonding or adhesive bonding, are because of their fibrous nature compatible with the topsheet and can be firmly bonded thereto using relatively small amounts of glue. Since the topsheet is connected to the backsheet via the fibers of the elastic member, which preferably comprises a second layer of fibers at the side of the backsheet, a certain amount of independent movement of the topsheet and backsheet is possible. When the absorbent article is stretched in a direction having a componenet which is perpendicular to the main direction of stretch, which will be generally parallel to the side along which the elastic member is applied, the topsheet and the backsheet can adjust their relative positions to the stretch. By this, less buckling of the topsheet and backsheet takes place, hence reducing chances of leakage along the elastic member.

An embodiment of an absorbent article according to the invention which comprises two side panels located at respective end-parts of the longitudinal sides and extending transversely thereto, is characterized in that at least one side panel comprises an elastic member.

The side panels that connect the back lateral side of the absorbent article with the front lateral side, are during movement of the user of the diaper subject to stretch in many different directions. During this movement it is important that the side panels remain in a position which is adjacent to the body of the user in order to prevent leakage of body fluids along the side panels. When in a diaper the topsheet, the backsheet and the elastic substrate are laminated via the layers of fibers that are pre-bonded to the substrate, the side panels can stretch in many directions, with relatively small amounts of buckling, a property which is especially desirable for the side panels. The same applies for side panels in training pants or incontinence briefs in which the elastic members are only connected to the body-facing side of the backsheet.

Another embodiment of an absorbent article according to the invention is characterized in that the elastic member is bonded to the backsheet, which is mechanically treated in the areas that are coextensive with the elastic member so that the backsheet is permanently elongated in those areas.

The backsheet, which is relatively inelastic, is in areas where elasticity is needed, provided with a permanent physical deformation. If the elastic member is laminated to both backsheet and a relatively non-elastic topsheet, the topsheet is also physically deformed in those areas. The permanent deformation can be imparted to the backsheet and the topsheet by passing the laminated structure of topsheet, backsheet and the elastic member between two engaging pressure rolls. The pressure rolls can permanently enlongate the topsheet and backsheet by stretching them beyond their range of elastic recovery. Upon relaxation after stretching, the topsheet and backsheet are gathered in crinkles by the elastic member. A method of producing laminates comprising a reticulated elastic member which is sandwiched between two non-elastic layers that are streched beyond their range of elastic recovery, is known from the American patent U.S. Pat. No. 4,525,407, which is hereby incorporated by reference.

Alternatively, one of the pressure rolls is provided with teeth that extend in an axial direction of the rolls, a second pressure roll being provided with matching recesses for receiving the teeth of the first roll. The teeth impart physical deformations to the backsheet and the topsheet that cause an intermittent thinning of the material so that a crinkled structure is obtained that can elongate along a certain range. Especially using this method of elongation, which is described in detail in the American patent application Ser. No. 07/662,537 of Feb. 28, 1991 now U.S. Pat. No. 5,156,793 in the name of the Procter & Gamble Company (case 4340), the topsheet and the backsheet can be thinned to the point of rupture, so that the fluid-impermeability of the backsheet is lost. According to the above mentioned patent application, the elastic member can be formed by a natural rubber foam strip, which is fluid-impermeable so that no leakage occurs through the backsheet even after rupture thereof.

With respect to rubber foam strips, use of an elasic member that comprises a net-like elastic structure to which a fibrous layer is attached, between the deformed parts of the topsheet and the backsheet, results in an increased resistance against delamination of the topsheet, the backsheet and the elastic member. For a good bondstrength between the topsheet and the fibers of the elastic member, a relatively small amount of glue is necessary.

In the areas where the the topsheet is thinned to a large extent, the fibers of the elastic member provide sufficient bulk to ensure a comfortable and soft feeling to the user's skin. The fibrous nature of the elastic member allows liquids on the skin of the user, such as sweat, to evaporate. By using hydrophobic fibers, the side panels can be made liquid-repellant thus giving a dry feeling upon contact with the user's skin.

Again another embodiment of an absorbent article according to the invention is characterized in that both sides of the substrate are covered by a layer of fibers, the fibers on one side of the substrate being orientated transversely to the fibers on the other side of the substrate.

The fibers connected to the elastic substrate which are orientated in the direction of stretching, disentangle upon stretching of the substrate. Fibers that are orientated transversely to the direction of stretching of the substrate, will upon stretching of the substrate be pulled apart so that voids among the fibers may occur. Conversely, between the fibers that are orientated in the direction of stretching, no voids will occur. Upon movement of the user, the voids can be filled with body fluids which can be released from the voids upon application of pressure.

However, by entangling the fibers on one side of the substrate in a first direction which is generally parallel to the direction of stretch and entangling the fibers on the other side of the substrate transversely thereto, the substrate can be stretched without voids occurring. At the same time, the fibers orientated perpendicularly to the direction of stretch improve the flexibility of the combined topsheet, backsheet and elastic member so that it can easily flex out of the plane of the direction of stretch.

Again another embodiment of an absorbent article according to the invention is characterised in that the fibers are mutually bonded.

Fibers on one side of the elastic substrate can be bonded to other fibers on the same side of the substrate and to fibers on the other side of the substrate, for instance by contacting the fibers with hot air. Thermal bonding increases the adhesion of the fibers among themselves so that the chance of detachment of the fibers from the substrate is reduced and the delamination strength of the topsheet and the backsheet is increased. Thermal bonding of the fibers can be achieved by passing the elastic substrate and the fibers trough a pressure nip of two hot calendar rolls or for instance by passing hot air along the fibers.

BRIEF DESCRIPTION OF THE DRAWINGS

Some embodiments of an absorbent article according to the invention will be described in detail in accordance with the accompanying drawings in which.

DETAILED DESCRIPTION OF THE DRAWINGS

Figure 1:
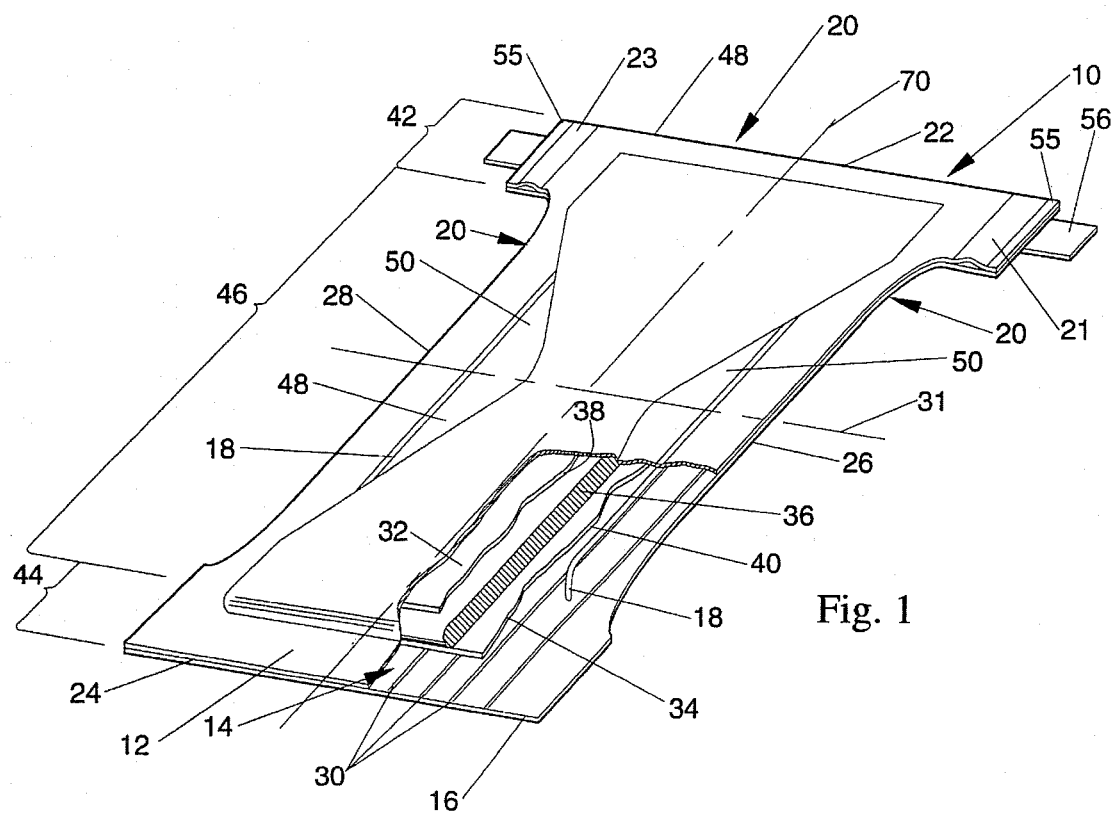
FIG. 1 shows a perspective, partial cut-away view of a disposable absorbent article according to the invention.

In the drawings, the described embodiments of the absorbent article refer in detail to a disposable diaper which is to be discarded after a single use. The invention is however not limited to disposable diapers but also relates to incontinent briefs, training pants and and other absorbent structures wich are drawn up between the legs and worn around the waist.

FIG. 1 shows a known diaper 10 in its flattened, ie, two-dimensional state, before it is placed on the diaper wearer. The diaper comprises a permeable topsheet 12, an absorbent core 14, a liquid-impermeable backsheet 16 and elastic members 18, 21 and 23 placed between the topsheet 12 and the backsheet 16. The elastic member 18 may be assembled in a known configuration as is described in the American patent U.S. Pat. No. 3,860,003 which is incorporated herein by reference. In the embodiment shown in FIG. 1, the topsheet 12 and the backsheet 16 are coextensive and have length and width dimensions generally larger than those of the absorbent core 14. The topsheet 12 is superposed on the backsheet 16 thereby forming a periphery 20 of the diaper. The periphery 20 comprises two longitudinal sides 26 and 28 and two lateral sides 22 and 24. The topsheet may be affixed to the backsheet 16 in any suitable mannner as is well known in the diaper manufacturing art. A multiplicity of longitudinal adhesive bands 30 can be applied along the full length of the backsheet 16 generally parallel to the longitudinal centerline 70 of the backsheet 16. The extent and location of the points where the topsheet 12, the backsheet 16 and the longitudinal adhesive bands 30 come together will depend on the spacing between the longitudinal adhesive bands 30 and on the distance the topsheet 12 and the backsheet 16 extend beyond the absorbent core 14. A hot-melt adhesive suitable for use as longitudinal adhesive bands 30 is manufactured by Eastman Chemical Products Company, of Kingsport, Tenn. and marketed under the tradename Eastobond A-3. It is of course possible to affix the topsheet to the backsheet in other ways, such as for instance via an intermediate member.

The diaper 10 comprises first and second waist portions 42 and 44 extending, respectively, form the first lateral side 22 and the second lateral side 24 of the diaper periphery 20 toward the lateral centerline 31 a distance from about ⅕ to about ⅓ the length of the diaper 10. The waist portion 42 comprises two side panels 55 of the diaper, which, when the diaper is worn, encircle the waist of the wearer together with the side portions of the waist portion 44. The side panels 55 of the waist portion 42 each comprise an elastic member 21,23, which can consist of a piece of crosslinked natural rubber foam according to the non-published American Patent application Ser. No. 07/662,537 of Feb. 28, 1991 now U.S. Pat. No. 5,156,793 in the name of The Procter & Gamble Company (our Case 4340). In the side panels 55 according to the invention, the elastic members 21,23 comprise an elastic substrate to which at least one layer of fibers is pre-bonded, of the type as shown in FIG. 2.

The crotch portion 46 of the diaper 10 is that portion between first and second waist portion 42 and 44, and comprises that portion of the diaper 10 which, when worn, is positioned between the legs of the wearer and covers the lower torso of the wearer. The absorbent core 14 may be any means which is generally compressible, conformable, non-irritating to the wearer's skin, and which is capable of absorbing and retaining liquids. A preferred absorbent core 14 has first and second opposed faces 32 and 34 respectively and comprises an absorbent layer 36 and first and second tissue layers 38 and 40, respectively. The first and second tissue layers 38 and 40 overlay the major surfaces of the absorbent layer 36.

The absorbent layer 36 is intended to absorb and contain liquid and may be manufactured in a wide variety of sizes and shapes (e.g., rectangular, hourglass, etc.) and from a wide variety of liquid absorbent materials commonly used in disposable diapers, such as comminuted wood pulp which is generally referred to as airfelt. Other liquid absorbing materials may also be used in the manufacture of the absorbent layer 36 such as a multiplicity of plies of creped cellulose wadding, absorbent gelling material, absorbent foams or sponges, or any equivalent material or combination of materials. The total absorbent capacity of the absorbent layer 36 should, however, be compatible with the design liquid loading in the intended use of the disposable diaper 10.

Further, the size and absorbent capacity of the absorbent layer 36 may be varied to accomodate wearers ranging from infants through adults. The embodiment of diaper 10 illustrated in FIG. 1, has an hourglass shaped absorbent layer 36, and is intended to be worn by infants ranging in weight from 5 kgs. to about 12 kgs. (12 to about 26 pounds). The absorbent layer 36 is, therefore, a battt of airfelt approximately 41 cm (16 inches) long when measured along the longitudinal centerline, approximately 32 cm (12 inches) across the lateral sides 22 and 24, and approximately 10 cm (4 inches) across the narrowest part of the crotch portion 46. The absorptive capacity of the airfelt used for the absorbent layer 36 is sufficient to absorb and retain from about 8 to about 16 grams of water per gram of absorbent material. Accordingly, the airfelt used in the preferred embodiment shown in FIGS. 1 and 2 weighs from about 30 to about 56 grams and has a generally uniform caliper. It should be understood, however, that the size, shape, configuration, and total absorbent capacity of the absorbent layer 36 may be varied to accommodate wearers, ranging from infants through adults. Therefore, the dimensions, shape, and configuration of the absorbent layer 36 may be varied (e.g. the absorbent layer 36 may have a varying caliper, or a hyrophilic gradient, or may contain absorbent gelling materials).

The first and second tissue layers, 38 and 40, are intended to improve the tensile strenght of the absorbent core 14 and to reduce the tendency of the aborbent layer 36 to split, lump or ball when wetted. The first and second tissue layers, 38 and 40, also help to improve lateral wicking of liquids, thereby providing a more even distribution of liquid in the abosrbent layer 36. While a number of materials and manufacturing techniques may be used to manufacture the first and second tissue layers, 38 and 40, satisfactory results have been obtained with sheets of tissue paper having a basis weight of approximately 16 grams per square meter (10 pounds per 3000 square feet) and having an air permeability of approximately 30 cubic meters per minute per square meter (100 cubic feet per minute per square meter) over 13 mm (0.5 inch) water pressure drop. While the first and second tissue layers, 38 and 40, are preferably coterminous with the absorbent layer 36, they may have different dimensions, a different configuration, or they may be omitted entirely.

The absorbent core 14 is superimposed on the backsheet 16 and is preferably affixed thereto by any means as is well known in the diaper art. For example, the absorbent core 14 may be secured to the backsheet 16 by a uniform continuous layer of adhesive, a patterned layer of adhesive, or an array of lines or spots of adhesive. In the preferred embodiment illustrated in FIGS. 1 and 2 the longitudinal adhesive bands 30 are used to affix the absorbent core 14 to the backsheet 16.

The backsheet 16 is impermeable to liquids and prevents liquids absorbed by the absorbent core 14 from wetting the undergarments, clothing, bedding, and other objects which contact the wearer of the disposable diaper 10. Preferably the backsheet 16 is a polyethylene film of from about 0.012 to about 0.051 mm (0.0005 to about 0.0002 inches) thick, although other flexible, liquid permeable materials may also be used. As used herein, the term "flexible" refers to materials which are compliant and which readily conform to the shape and contours of the human body. A suitable polyethylene film, for use in combination with elastic members in their pre-stretched state, is manufactured by Monsanto Chemical Company and marketed in the trade as Film No. 8020. The backsheet 16 is preferably embossed and/or matte finished to provide a more clothlike appearance. Further, the backsheet 16 may have passages which permit vapors to escape from the absorbent means 14 while still preventing liquid from passing through the backsheet 16.

In an embodiment, the backsheet 16 has a modified hourglass shape extending beyond the absorbent layer 36 a minimum distance of at least about 1.3 cm (0.5 inches) around the entire diaper periphery 20.

The topsheet 12 is compliant, soft feeling, and non-irritating to the wearer's skin and prevents the wearer of the diaper 10 from contacting the absorbent core 14. Further, the topsheet 12 is liquid permeable permitting liquids to readily penetrate through its thickness. A suitable topsheet 12 may be manufactured from a wide range of materials, such as natural fibers (e.g., wood or cotton fibers), synthetic fibers (e.g., polyester, polyethylene, polypropylene), or a combination thereof. Alternatively, the topsheet 12 may be a foam, such as the reticualted foams which are well known in the art or any of the formed films which are also well known in the art.

A number of manufacturing techniques can be used to manufacture the topsheet 12. For example, the topsheet 12 may be woven, nonwoven, spunbonded, carded, or the like. A preferred topsheet 12 is carded, and thermally bonded by means well known to those skilled in the nonwoven fabrics art. Preferably the topsheet 12 has a weight of from about 15 to 21 grams per square meter, a minimum dry tesile strength of at least about 400 grams per centimeter in the machine direction and a wet tensile strength of at least about 55 grams per centimeter in the cross machine direction.

The elastic members 18 are affixed to the diaper 10 along both longitudinal marginal portions 50 so that they tend to draw and hold the diaper 10 against the legs of the wearer. Thus, when worn the diaper 10 will have elasticized leg openings. This result may be accomplished by any of several means as are well known in the diaper art. A diaper construction incorporating elastic strips is described in detail in the hereinabove referenced U.S. Pat. No. 3,860,003. In addition, a method and apparatus suitable for manufacturing a disposable diaper having elastic leg bands are described in U.S. Pat. No. 4,081,301 entitled "Method and Apparatus for Continuously Attaching Discrete, Stretched Elastic Strands to Predetermined Isolated Portions of Disposable Absorbent Products" which issued to K. B. Buell on Mar. 28, 1978 and which patent is incorporated herein by reference.

Relating the teachings of U.S. Pat. No. 3,860,003 to the embodiment shown in FIG. 1, it can be seen the elastic members 18 are operatively associated with both longitudinal marginal portions 50 in the crotch portion 46 in an elastically contractible condition so that in a normally unrestrained configuration the elastic members 18 effectively contract or gather the longitudinal marginal portions 50.

In the embodiment illustrated in FIG. 1, the elastic members 18 are affixed to a portion of the backsheet 16 in the longitudinal marginal portions 50. A suitable adhesive will be flexible and of sufficient adhesiveness to hold the elastic member 18 to the backsheet 16 while the elastic member 18 is stretched. An adhesive which has been used with satisfactory results is manufactured by Findley Adhesives Corporation of Elm Grove, Wis. and is marketed under the tradename Findley 581-334-01.

The elastic members 18 can be operatively associated with the longitudinal marginal portions 50 in at least three ways. For example, the elastic member 18 may be stretched and while in the stretched condition affixed to the uncontracted and unstretched longitudinal marginal portions 50. Alternatively, the longitudinal marginal portions 50 may be contracted (e.g., by pleating) and then affixing the unstretched elastic member 18 to the contracted longitudinal marginal portions 50.

Another way of inserting the elastic members 18 between the topsheet 12 and the backsheet 16 is to first affix the elastic members between the topsheet 12 and the backsheet 16 in a non-stretched state and then to mechanically deform the topsheet and the backsheet in the marginal portions 50. The deformation imparts a stretchability to the normally non-extendable topsheet and backsheet. This method is especially advantageous when as an elasctic member, a net-like elastic substrate is used to which at least one layer of fibers is pre-bonded. When the topsheet becomes relatively thin upon imparting a deformation thereto, the elastic member as shown in FIG. 2 is due to its fibrous nature soft and bulky enough to prevent an uncomfortable pressure being exerted to the wearer's skin. Due to the layer of fibers between the elastic net-like substrate and the topsheet, a good breathability is maintained.

The elastic member 18 preferably produces a tensile force of about 100 grams when stretched 100 percent from its relaxed condition.

The diaper 10 is provided with an outer fastening means 56 for maintaining the first and second waist portions 42 and 44 in an overlapping configuration when the diaper 10 is worn. Thus, the diaper 10 is fitted to the wearer and a side closure formed.

More specifically, the outer fastening means 56 affixes the first waist portion 42 to the second waist portion 44 thereby maintaining the first and second waist portions 42 and 44 in an overlapping configuration. Thus, the outer fastening means 56 must be affixed to both the first waist poriton 42 and to the second waist portion 44 in a manner and with a strength that is sufficient to resist the forces acting to cause the first and secons waist portions 42 and 44 to separate during wearing.

The outer fastening means 56 may comprise any of the well known means for achieving a side closure such as Velcro strips or patches, buttons, or snaps. A preferred outer fastening means 56 is an adhesive tape as is well known in the diaper art.

Any of the well known configurations and constructions may be used as the adhesive tape. For example, the adhesive tape may be a single use tape or a multiple use tape (i.e., refastenable). A preferred adhesive tape is a Y-shaped tape as described in detail in U.S. Pat. No. 3,848,594 entitled Tape Fastening System for Disposable Diaper which issued to K. B. Buell on Nov. 19, 1974, which patent is incorporated herein by reference. The outer fastening means 56 are provided at both side panels.

Figure 2A:
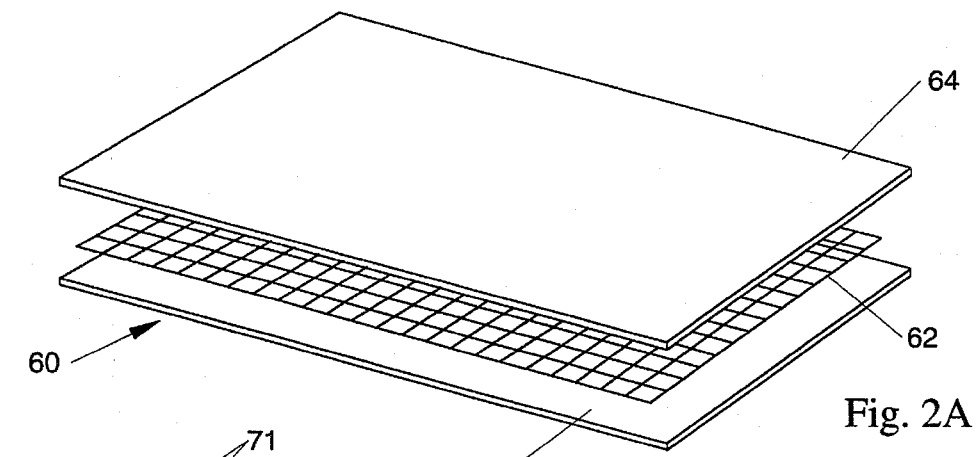
FIG. 2A shows a perspective view of an elastic member.
Figure 2B:
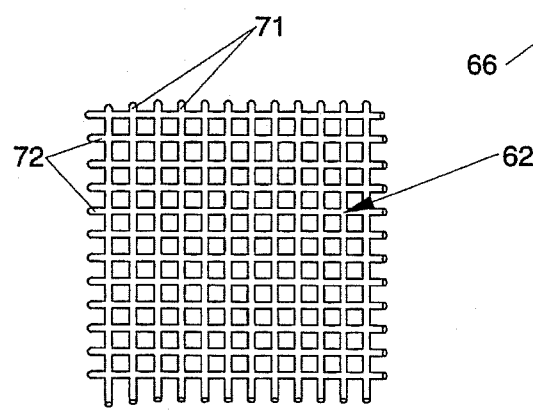
FIG. 2B shows a plan view of an elastomeric net.

FIG. 2A shows the elastic member 60 comprising the net-like elastic substrate 62 which is on both sides provided with a layer of fibers 64 and 66. FIG. 2B shows the the elastic substrate or elastomeric net 62 which comprises interconnected elastic strands 71 and 72. The fibers are bonded to the substrate 62 by passing the substrate and the fibers under a row of manifolds and directing jets of water through the fibers, a diameter of the jets being about 0.1 mm at a pressure of between 1 and 10 atm. A desired peelstrength of the layers of fibers 64 and 66 for use as elastic member in the side panel 55 of the diaper 10 has between 2N and 8N, preferably between 5N and 6N.

For use in a side panel 55, the elastic member 60 has the following properties:

The caliper of the elastic member for use in the side panels 55 lies at a pressure of 17.1 g/cm$^2$, between 1 and 3 mm, preferably between 1.3 and 1.8 mm.

The thickness of the elastic substrate's strands under a pressure of 17.1 g/cm2, lies between 0.05 and 2.00 mm, preferably between 0.08 and 1.00 mm in the direction of the longitudinal sides (machine direction) and between 0.1 and 2.50 mm, preferably between 0.15 and 1.00 mm in the direction of the lateral sides (cross machine direction).

The basic weight of the fibers that are bonded to the elastic net-like substrate 62, lies between 35 and 100 g/m$^2$, preferably between 50 and 70 g/m$^2$.

The basic weight of the elastic substrate lies between 20 and 250 g/m$^2$, preferably between 70 and 150 g/m$^2$.

The fibers that are bonded to the substrate can be made of polyolefins, polyethylene or polypropylene copolymers, polyester, acrylic fibers, rayon fibers or natural fibers such as wood pulp fibers, cotton or viscose, or combinations thereof.

The elastic substrate 62 can be made of sythetic elastomers, such as styrene-butadiene rubber, polybutadiene, polyisoprepene, polychloropropene (e.g. Neoprene), ethylene-propylene, fluorinated elastomers, or thermoplastic elastomers or combinations thereof. Suitable thermoplastic elastomers are styrene-diene block copolymers of the A-B-A' type, wherein A and A' may be identical or different blocks. Examples of copolymers of this type are styrene-butadiene-styrene (SBS), sold under the trade name Kraton 1101 by Shell, or styrene-isopre-styrene (SIS) or mixtures of SIS/SBS.

The elastic substrate 62 has a number of strands per inch of 2 to 40, preferably of between 4 and 15 in the direction of the longitudinal sides (machine direction) and of between 3 and 40, preferably between 3 and 25 in the direction of the lateral sides (cross machine direction).

The angle of intersection of the strands is between 30° and 150°, preferably between 70° and 110°.

The tensile properties of an elastic member 60 for use in the side panels 55 are summarized in Table I, useful elastic members having tensile properties as listed in column 3, the preferred elastic members having tensile properties as listed in column 4.

Since the fibers that are bonded to the substrate disentangle upon first stretching of the elastic member from its relaxed state to, for instance, an elongation of 100% (first load cycle), the tensile force upon stretching differs more from the tensile force upon relaxation (first unload cycle) than would be the case in the absense of fibers. Also is the tensile force exerted by the elastic member during the first load cycle and unload cycle higher than during the second and subsequent load and unload cycles. By the first stretching, the elastic member is 'activated' so that the tensile properties are best represented by the tensile force values for the second load and unload cycle.

TABLE I

Tensile properties of elastic member 60.

| Cycle | Elongation (%) | Tensile Force (N/inch) | Preferred Tensile Force (N/inch) |
|---|---|---|---|
| First Load Cycle | 25 | 1.00–2.50 | 1.50–2.00 |
|  | 50 | 1.75–3.75 | 2.40–3.10 |
|  | 75 | 2.50–4.80 | 3.20–4.10 |
|  | 100 | 3.50–6.00 | 4.20–5.30 |
| First Unload Cycle | 25 | 0.20–1.20 | 0.50–0.90 |
|  | 50 | 0.65–2.65 | 1.35–1.95 |
|  | 75 | 1.40–3.70 | 2.15–2.95 |
|  | 100 | 2.90–5.40 | 3.65–4.65 |
| Seond Load Cycle | 25 | 0.30–1.50 | 0.65–1.15 |
|  | 50 | 0.95–2.95 | 1.60–2.30 |
|  | 75 | 1.75–4.05 | 2.45–3.35 |
|  | 100 | 2.95–5.45 | 3.65–4.75 |
| Second Unload Cycle | 25 | 0.15–1.15 | 0.45–0.85 |
|  | 50 | 0.60–2.60 | 1.30–1.90 |
|  | 75 | 1.35–3.65 | 2.10–2.90 |
|  | 100 | 2.70–5.20 | 3.45–4.45 |

For a preferred elastic member, the stretch creep, the percentage set, the air-permeability, the buckling and the delamination force were mesured by the methods described herebelow. The elastic member under test had the following dimensions:

Caliper: 1.4–1.5 mm under a pressure of 17.1 g/cm$^2$ Strand thickness at a pressure of 17.1 g/cm$^2$:

0.10–0.15 mm in the direction of the longitudinal sides (MD)

0.25–0.30 mm in the direction of the lateral sides (CD)

Basic weight of the fibers: 60 g/cm$^2$. To each side of the substrate a layer of fibers was connected.

Basic weight of the net-like substrate: 110 g/m$^2$

Composition of the net-like substrate: a mixture of SBS/SIS Number of strands per inch: 12 in the direction of the longitudinal sides (MD), 9 in the direction of the lateral sides (CD), Angle of inersection of strands: 90°.

Stretch creep

The stretch creep of the elastic member was measured at a temperature of 38° C. by affixing a weight of 200 g to the elastic member leaving it in the stretched condition for 30 minutes. After 30 minutes the weight was removed and the elastic member was allowed to relax for 30 seconds. The increase in length of the elastic member before and after stretching is the amount of creep, which was found to be about 35%. For the elastic members, that are used in the side panels, or as leg elastics or waist-elastics, it is desirable that the creep is as low as possible (ideally 0%) and is not higher than 35%.

Percentage set

The percentage set was measured in the following manner: The elastic member was in a first load cycle extended in a tensile tester at a crosshead speed of 500 mm min$^{-1}$ to 100% elongation and held for 30 seconds. Thereafter, the elastic member was in the first unload cycle allowed to relax at the same speed. At the end of the unload cycle the elastic member was allowed to rest for 60 seconds, after which the process was repeated during a second load/unload cycle. The percentage set is the relative increase in length after a cycle. For the elastic member under test, the percentage set was about 15%. Ideally the percentage set is 0%. For elastic members for use in the side panels, leg elastics or waist elastics, the percentage set should remain below 15%.

Air permeability

The air permeability of the elastic member was measured by clamping a sample of the elastic member in its unstretched state over an orifice and blowing air through the elastic member at a constant pressure drop of 125 Pa. The apparatus used for testing the air permeability consisted of a portable air permeability tester, Model V, manufactured by Albany Engineered Systems, P.O. Box 310, Glen Falls, N.Y. 12801 or an Air Flow Tester, Model 9025, manufactured by United States Testing Co., Inc., 1415 Park Ave., Hoboken, N.J. 07030.

For the elastic member having the above mentioned properties, the air permeability was found to be 23.32 m3 per minute, per square meter of orifice size {m$^3$/(min.m$^2$)}. In contrast, for an elastic member comprised of a strip of cross linked natural rubber foam, an air permeability of 1.05 m$^3$/(min.m$^2$) was found. For applications in absorbent articles, the elastic members preferably have an air permeability of between 5 and 43 m$^3$/(min.m$^2$) and most preferably between 15 and 30 m$^3$/(min.m$^2$).

Buckling

The buckling of the elastic member was tested by visually observing the angle at which wrinkles occured in the elastic member upon application of a shear force. In the test method the elastic member was first stretched to disentangle the fibers so that the elastic member has the elastic properties of the second and subsequent load- and unload cycles as tabulated in Table I. A patch of 10 cm by 10 cm was with one side parallel to the machine direction, taped to a horizontal surface. The opposite side of the elastic member in the machine direction was fixed to a ruler along its entire length so that the free length in the cross machine direction was 8 cm. Then the ruler was moved in the cross machine direction by x cm to elongate the elastic member by a predetermined percentage. The percentage elongation, $\Delta$, is defined as $$\Delta = \frac{Lo+x}{Lo}$$

wherein Lo is the free length of the sample in the cross machine direction in the relaxed state. In the stretched state of the elastic member, the ruler was moved in the machine direction by a distance y while keeping the percentage stretch constant. The distance y by which the ruler was moved in the machine direction until wrinkles in the elastic member were observed, is a measure for the buckling at a given percentage elongation $\Delta$. Also the angle $\theta$ between the cross machine direction and the side of the elastic member that extends from a corner which is fixed to the horizontal surface to an opposite corner fixed to the ruler, is a measure for the buckling. Herein is $\theta$ equal to $$\arctan\left(\frac{y}{Lo+x}\right)$$

In table II the angle $\theta$ is given for the elastic member and for an equally sized sample of cross linked natural rubber foam for different percentages of elongation.

TABLE II

Buckling of the elastic member and equal sized sample of cross linked natural rubber foam for different elogations

| $\Delta$ (%) | $\theta$ (degrees) Elastic member | $\theta$ (degrees) (cross linked natural rubber foam) |
|---|---|---|
| 0 | 30 | 5 |
| 20 | 37 | 25 |
| 40 | 37 | 31 |
| 60 | 45 | 42 |
| 80 | 47 | 53 |

The measuring error in the angle $\theta$ is believed not to be higher than 3 degrees. During use in side panel, the percentage elongation $\Delta$ is between 15 and 20% and does not exceed 40%. In this range of elongation, the elastic member according to the invention shows less buckling than a similar patch of cross linked natural rubber foam, resulting in increased fit and reduced leakage along the side panels. For use of the elastic member in a side panel of an absorbent article desirable buckling properties are:

at 0% elongation: 0°<$\theta$<55°, preferably 30°<$\theta$<45°,
at 20% elongation: 0°<$\theta$<60°, preferably 37°<$\theta$<50°,
at 40% elongation: 0°<$\theta$<70°, preferably 37°<$\theta$<60°.

Since buckling is to an important extent determined by the mesh size of the elastic substrate, the mesh size should be chosen for an elastic member in a side panel so as to give the preferred range of angles for buckling.

Delamination

A delamination test was done for the elastic member having the above mentioned properties, the fibers after hydro-entangling having been mutually thermally bonded by air-through bonding. In the test method a finished side panel comprising an elastic member having the above mentioned properties, was glued between the backsheet and the topsheet unsing a cold transfer glue. A strip of 25 mm in the cross machine direction and 75 mm in the machine direction was cut from the side panel. At one end, the topsheet and the backsheet were delaminated by 5 mm in the machine direction. The sample was then placed in a tensile tester with the topsheet and the backsheet in the upper and lower jaws of the tester respectively. At a crosshead speed of 500 mm/min. the average force was recorded to completely delaminate the sample. For the side panel comprising the elastic member of which the fibers were thermally bonded, the delamination force amounted to 5.3N. For a similar side panel comprising an elastic member of which the fibers were not bonded, except by hydroentangling, the delamination force for separation of topsheet and backsheet was 3.2N.

The thermal bonding of the fibers of the elastic member, that adheres strongly to topsheet and backsheet, results in an increase in strength of the side panel by 40% compared to when the fibers are not thermally bonded.

In a side panel comprising the elastic member according to the invention the delamination force of the topsheet and the backsheet preferably lies between 2N and 8N, most preferably between 5N and 6N.

Figure 3:
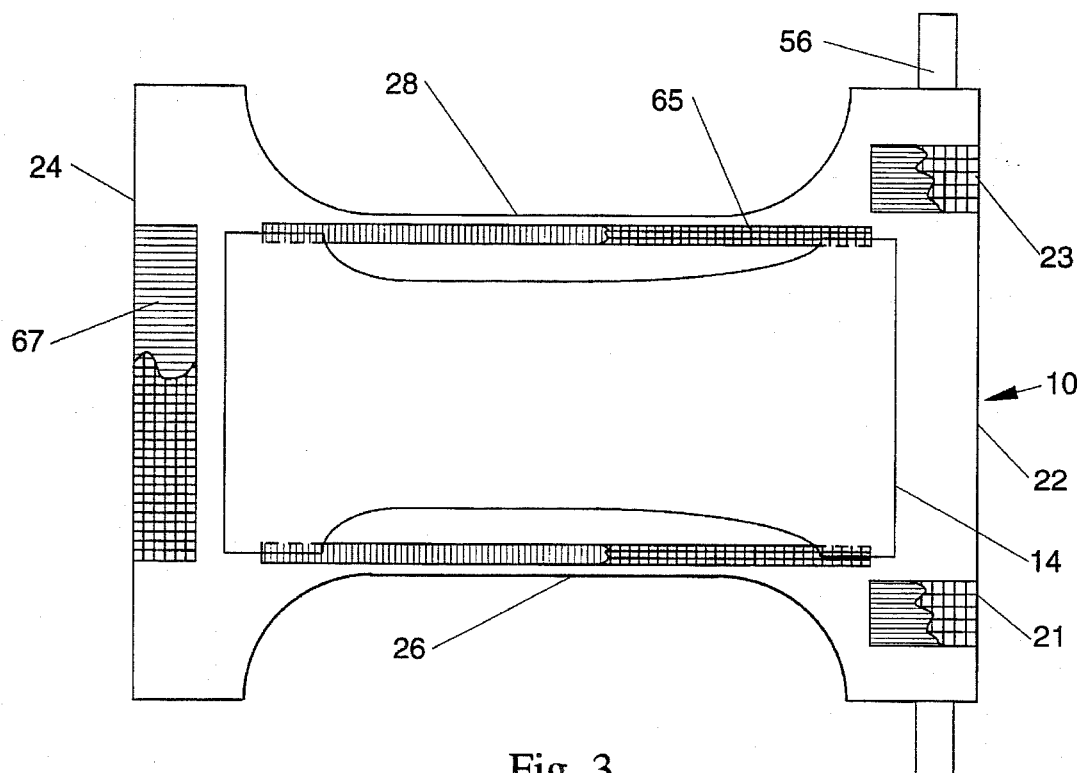
FIG. 3 shows an absorbent article provided with elastic side portions, an elastic waist-portion and elastic leg cuffs comprising the elastic member of FIG. 2

FIG. 3 shows the positions in the diaper 10 in which the elastic member as described in FIG. 2 can be used. The elastic member can be part of the side panels 55, it can be placed along the longitudinal sides 26 and 28 of the diaper to form an elastic leg cuff or can be placed along a transverse side 24 to form an elasic waist part. The elastic member 60 can be placed between the topsheet 12 and the backsheet 16 in a stretched condition, so that upon relaxation of the elastic member, the topsheet and the backsheet are gathered. Alternatively, the elastic member 60 is unstretched, the topsheet 12 and the backsheet 16 being bonded to the elastic member in a compressed state.

In a preferred embodiment, the elastic member is placed between the topsheet and the backsheet in a condition of substantially zero strain of topsheet, backsheet and the elastic member. The areas of the diaper 10 where the elastic member is laminated between the the topsheet 12 and the backsheet 16, are after lamination of the topsheet to the backsheet, permanently elongated, for instance by contacting the areas of the side panels 55, of the leg elastics 65 and of the waist elastic 67 with a set of intermeshing teeth. In this way an amount of stretch can be imparted to the diaper in pre-selected areas, the amount of stretch being controllable by the length of the area along which deformation takes place, the spacing of the intermeshing teeth and the like. The elastic member 60 can be used in either one of the elastic side panels 55, the leg portions 65 and the waist portion 67, separately and in combination with other, well known, elastic means, or in combination with one another.

Although the meshes of the substrate 60 of FIG. 2 are rectangular, other shapes of meshes can be applied, such as diamond-shaped, triangular or parallellogram-shaped meshes. The latter is advantageous in the side panels, since the force exerted on the side panels when a diaper is applied to an infant, is found in practise to lie not exactly parallel with the lateral sides 22 and 24. A substrate for use in the side panels 55, preferably consists of two sets of parallel strands, one set of strands extending generally parallel to the longitudinal sides 26 and 28 of the diaper 10, the other set of strands intersecting the first set at an angle of between 60° and 90°.

In the side panels 55, the strands of the substrate 62 that extend in the direction generally parallel to the longitudinal sides 26 and 26 can be of relatively low elasticity compared to the strands extending generally parallel to the lateral sides 22 and 24 and can amount for instance to not more than 10% recoverable elongation upon exertion of a force of between 300 and 900 g.

Figure 4:
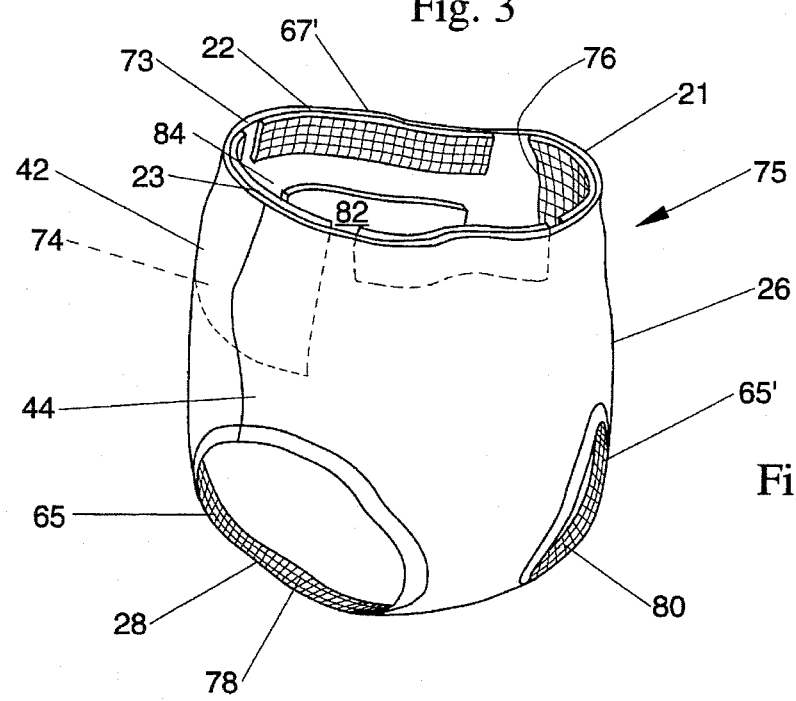
FIG. 4 shows an absorbent article in the form of a training pants or an incontinence briefs, comprising the elastic member of FIG. 2.

FIG. 4 shows an absorbent article such as a training pants 75, or adult incontinence briefs, such as described in detail in the American patent U.S. Pat. No. 5,074,854. The backsheet of the training pants 75 is of genereally similar form as the backsheet 16 of the diaper 10 as shown in FIG. 1, and is indicated in FIG. 4 by the same reference numeral. For other structures of the training pants 75 that are similar to structures of the diaper 10, like reference numerals are used. In the training pants 75, the end parts 42 and 44 of each of the longitudinal sides 26 and 28 are joined in side panel areas 74 and 76 during manufacturing. The lateral sides 22 and 24 form an endless waistband 73. The parts of the longitudinal sides that are located between the end parts 42 and 44 form two leg cuffs 78 and 80, encircling the legs of the wearer.

Elastic members 67 and 67' can be placed in the waistband 73, elastic members 65 and 65' can be placed in the leg cuffs 78 and 80 and elastic members 21 and 23 can be placed in the side panel areas 74 and 76 of the training pants 75. In the training pants 75 of FIG. 4, the absorbent core 82 and the topsheet covering the core, are smaller than the backsheet 16, which extends beyond the perimeter of the core and topsheet. The elastic members that are connected to the body facing side 84 of the backsheet 16, provide soft and resilient fibrous contact areas to the wearer's skin. Preferalby the fibers are in this case thermally bonded to prevent detachment of the fibers from the elastic substrate. It is of course possible to use in the training pants 75 a larger topsheet, covering the elastic members, or to cover each of the elastic members by a single or a respective cover layer. In this case, the chance of detachment of fibers from the elastic substrate is reduced.

What is claimed is:

1. Absorbent article comprising:

a topsheet, a liquid impervious backsheet joined to the topsheet, an absorbent core disposed between the topsheet and the backsheet, a periphery of the absorbent article comprising two longitudinal sides and two lateral sides extending transversely to the longitudinal sides, and an elastic member connected to a body-facing side of the backsheet, the elastic member comprising an elastomeric net having a first side and a second side opposite said first side, a first layer of fibers joined to said first side of said elastomeric net, and a second layer of fibers joined to said second side of said elastomeric net, said first layer of fibers being oriented in a first direction and said second layer of fibers being oriented in a direction substantially perpendicular to said first direction.

2. Absorbent article according to claim 1 wherein the elastic member is positioned between the topsheet and the backsheet.

3. Absorbent article according to claim 1 wherein the first layer of fibers is entangled with the second layer of fibers.

4. Absorbent article according to claim 1 wherein the absorbent article comprises two side panels said side panel comprising said elastic member.

5. Absorbent article according to claim 1 wherein the backsheet is mechanically treated in an area that is coextensive with the elastic member.

6. Absorbent article according to claim 1 wherein the elastic member is attached to the backsheet in a prestretched state, the elastic member upon relaxation gathering the backsheet.

* * * * *